(12) United States Patent
Kong et al.

(10) Patent No.: US 7,396,644 B2
(45) Date of Patent: Jul. 8, 2008

(54) METHOD OF DIAGNOSING AND TREATING DENTINOGENESIS IMPERFECTA TYPE II BY USING DENTIN SIALOPHOSPHOPROTEIN GENE AND CODED PRODUCT THEREOF

(75) Inventors: Xiangyin Kong, Shanghai (CN); Shangxi Xiao, Shanghai (CN); Guoping Zhao, Shanghai (CN); Chuan Yu, Shanghai (CN); Landian Hu, Shanghai (CN)

(73) Assignee: Shanghai Institutes of Biological Science, Chinese Academy of Science, Shanghai (CN)

( * ) Notice: Subject to any disclaimer, the term of this patent is extended or adjusted under 35 U.S.C. 154(b) by 254 days.

(21) Appl. No.: 10/363,798

(22) PCT Filed: Aug. 30, 2001

(86) PCT No.: PCT/CN01/01292

§ 371 (c)(1),
(2), (4) Date: Mar. 5, 2003

(87) PCT Pub. No.: WO02/058722

PCT Pub. Date: Aug. 1, 2002

(65) Prior Publication Data

US 2003/0180280 A1    Sep. 25, 2003

(30) Foreign Application Priority Data

Sep. 5, 2000 (CN) ................. 00 1 25042

(51) Int. Cl.
*C12Q 1/68* (2006.01)
*C12P 19/34* (2006.01)

(52) U.S. Cl. .......................... 435/6; 435/91.2

(58) Field of Classification Search .................. None
See application file for complete search history.

(56) References Cited

OTHER PUBLICATIONS

Gu K, Chang S, Ritchie HH, Clarkson BH, Rutherford RB. Molecular cloning of a human dentin sialophosphoprotein gene.Eur J Oral Sci. Feb. 2000;108(1):35-42.*
Hacker et al (1997) Gut vol. 40, p. 623-627.*
Thisted et al (1998) What is a P-value?, available online at www.stat.uchigao.edu/~thisted.*
Deng et al (2001) Annals of Human Genetics, vol. 65, No. 3, pp. 313-329.*
Lucentini (2004) The Scientist, vol. 18, issue 24, p. 20.*
Zhang et al (2001) Nature Genetics, vol. 27 pp. 151-152.*
GeneCard for protein coding DSPP, avaialbe from www.genecards.org, pp. 1-9.*
MacDougall M., Eur J Oral Sci Jan. 1998; 106 Suppl 1:227-33, "Refined mapping of the human dentin sialophosphoprotein (DSPP) gene within the critical dentinogenesis imperfecta type II and dentin dysplasia type II loci."
Mary MacDougall et al. J Biol Chem 1997; 272(2):835-42, "Dentin Phosphoprotein and Dentin sialoprotein are cleavage products expressed from a single transcript coded by a gene on human chromosome 4."

* cited by examiner

*Primary Examiner*—Jehanne Sitton
*Assistant Examiner*—Stephen Kapushoc
(74) *Attorney, Agent, or Firm*—Merchant & Gould P.C.

(57) ABSTRACT

The invention has disclosed a method for diagnosis of dentinogenesis imperfecta type II (DGI-II) and/or dentinogenesis imperfecta type II with deafness (DGI-II with deafness). Said method comprises the steps of detecting the DSPP gene, transcript and/or protein in said subject and comparing it with the normal DSPP gene, transcript and/or protein to determine whether there is any variation, wherein said variation indicates that the possibility of suffering DGI-II and/or DGI-II with deafness in said subject is higher than the normal population. The present invention also discloses the method and pharmaceutical composition for treating DGI-II and/or DGI-II with deafness.

5 Claims, 4 Drawing Sheets

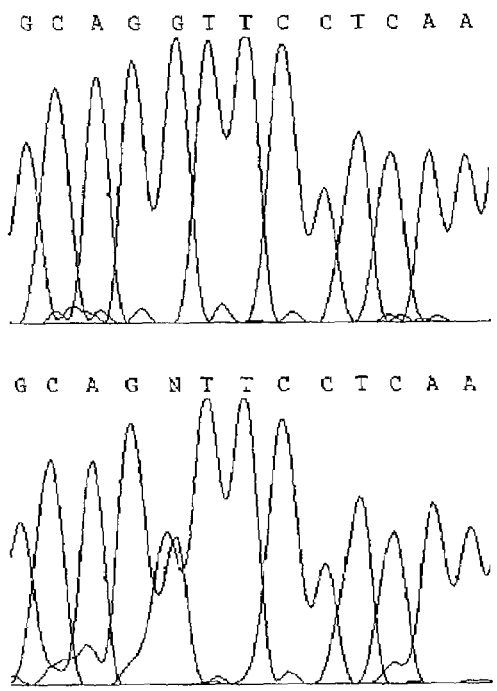
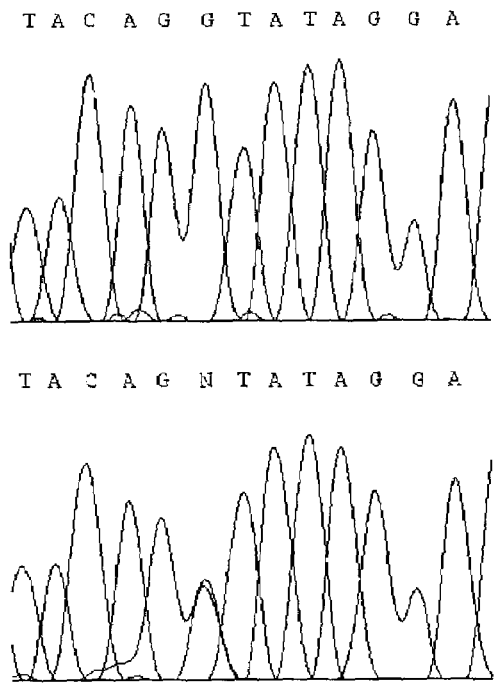
In Exon 3:
Codon: GTT → TTT
Amino acid: Val → Phe
Change of splicing site
... cagtattttctacttggcag ttt cct caa agc aaa ...
~~~~~~~~~~ V P Q S K
Intron 2           Exon 3
In Intron 3:
G → A
Change of splicing site
... aat gtg tca gta cag ataggatgtaat ...
N V S V Q ~~~~~~~~~
Exon 3           Intron 3
Fig. 4A
Fig. 4B

METHOD OF DIAGNOSING AND TREATING DENTINOGENESIS IMPERFECTA TYPE II BY USING DENTIN SIALOPHOSPHOPROTEIN GENE AND CODED PRODUCT THEREOF

FIELD OF INVENTION

This invention relates to both biological engineering and medical fields. In particular, it relates to a method of diagnosing and treating dentinogenesis imperfecta type II using human dentin sialophosphoprotein or DSPP gene and the coded product, and a pharmaceutical composition containing DSPP gene and/or protein.

TECHNICAL BACKGROUND

The odontoblasts produce the dentin, which consists in mature tooth or the tooth during tooth development phase. During dentinogenesis, the odontoblasts form dentinal tubules. Dentin cell processes in these tubules make dentin a living tissue. During the primary stage of dentinogenesis, the odontoblasts synthesize, secrete and re-absorb the dentin matrix components. Protein synthesis occurs within cells. Exocytosis and endocytosis occurs mainly in cell processes. The first material formed is unmineralized mantle dentin matrix, mainly including collagen secreted by cells and non-collagenous components. The fasciculata collagen fibers congregate to a ball structure. Due to the continual increase of new fibrils, collagen becomes closer and closer. As a result, these prophase collagen fibers change into collagen fibers. Thus predentin characterized by collagen matrix is formed. Later, the mineralization crystals gradually deposited to become dentin at some distance away from cells.

The mature dentin contains more inorganic minerals than the bone. 65 wt. % of dentin are minerals, mostly hydroxyapatite crystals. Organic materials are 20%, mainly collagenous proteins and non-collagenous proteins. These collagens offer braces to the deposition of hydroxyapatite plate like crystalline.

Type I collagen is predominant (about 97%) in dentin collagens, 10%-15% of which is type I collagen trimer. Different from other connective tissue, type III collagen is lacking in dentin. Moreover, there are types V and VI collagens in dentin, but the contents are small. Although the contents of non-collagenous proteins in dentin are small, there are various kinds. According to the source of proteins, the dentin noncollagenous proteins can be divided to four kinds: dentin specific protein, mineralized tissue specific protein, aspecific protein, and blood serum source protein (or dentin affinity protein). Dentin specific protein is the only one which is synthesized and secreted by odontoblasts and exists only in dentin. Mineralized tissue specific proteins means those that are found and exist not only in dentin but also in cementum and bone. They are synthesized and secreted by osteoblasts, odontoblasts and cementoblasts. The non-specific proteins exist both in dentin and other tissues, including parenchyma, and synthesized and secreted by odontoblasts and other kinds of cells. Blood serum source proteins are those which are synthesized by other cells in the body, mainly by liver cells, and secreted to serum. These proteins have a high affinity to dentin, though they are not synthesized by dentin. They can enter dentin by blood circulation, so they are also called dentin affinity proteins. Proteoglycans or PGS are other primary non-collagenous proteins in dentin. They are large covalent molecules formed by many anylose side chains and one core protein. These side chains are composed of repeating disaccharide chain units, each of which consists of one glycuronic acid and one N-acetamidoacetose. One function of PGS in dentinogenesis is to affect or even control the systematism of collagen skeleton in predentin. The dentin proteoglycans fixed on the solid bracket can induce the formation of hydroxyapatite in vivo and in physiologic pH and ionic condition in vitro. On the contrary, the liquid proteoglycans restrain the form of mineral components in vitro. The combination of PGS and $Ca^{2+}$ is the precondition of inducing the formation of hydroxyapatite.

Dentinogenesis imperfecta or DGI is an autosomal dominant dental genetic disease that has a prevalence of 1/8000. There are three types according to clinical taxonomy[1] (The number in brackets shows the relative literature.). Dentinogenesis imperfecta Type I is also named DGI-I. Except for dentinogenesis imperfecta, patients usually have osteogenesis imperfecta The pathogeny is broad mutations in collagen type I gene[2]. Type II or DGI-II is also called hereditary opalescent dentin. DGI-II has a relationship with the improper mineralization of dentin and its penetrance is nearly 100%[3]. Type III or DGI-III is also called dentinogenesis imperfecta Brandywine type or isolate hereditary opalescent dentin. It is a special hereditary opalescent dentin, only found in three isolates in Washington, D.C., the State of Maryland, USA. Witkop first reported this illness in 1956[4] and there is no related report in China till now. DGI-III has an obviously genetic heterogeneity. Its pathogeny is related to malamineralization. Because the gene causing DGI-I has been found and DGI-III is only found in the isolates in the State of Maryland, USA, DGI-II becomes the focus of tooth endodontics.

The clinical symptoms and pathology changes of DGI-II are as follows. The malajustment and turbulence of mineralization result in embryonic layer dysplasia in dentin. Both the primary dentition and permanent dentition are affected, with a more serious damage in primary dentition. A predominant feature is a blue-gray or amber brown discoloration of the teeth. The improper mineralized dentin is soft and the crown is prone to be worn. Moreover, compensatory hyperplasia of matrix increases in improperly mineralized dentin, leading to small or obliterated pulp chambers. Radiographs reveal that the affected teeth have bulbous crowns, narrow roots and small or obliterated pulp chambers and root canals. The pathology shows that the enamel surface is normal, but hypoplasia and hypocalcification can be found in about ⅓ of the patients. The enamel dentin junction changes greatly. Some teeth have a non-obvious sector structure in the enamel dentin junction. However, others are especially obvious. Dentin is lamellar with nearly normal outerdentin and dentinal tubules having subdivisional branches. In other parts, the dentin is obviously abnormal. Some short tubules or tubules with abnormal form distribute in dentin matrix disorderly. The predentin zone is very wide. Along the plywood, the remaining embedded cell can be seen, similar to embedded odontoblast and bloods. Observation under electron microscope indicates that the form and size of hypoplastic dentin microcrystal are unchanged, but the quantity is small. Uncalcified or partly calcified transverse collagen fasciculi and volumes of crystal space can be seen discontinuously.

For the mapping of DGI-II gene, in 1969, Bixler et al.[5] tried to use some protein polymorphic markers, such as ABO, Rh, MNSs, Kell, Fy, JK, HP, ACP1, PGM1 and PTC, to perform a linkage analysis in DGI-II families, but they failed to get the linkage evidence. In 1977, Mikkelsen et al.[6] mapped a group of specific components (GC) in Vitamin D conjugated protein to 4q11-q13. In the next year, Kühnl identified that GC included six phenotypes: GC2/2, 2/1+, 2/1−, 1+/1−, 1+/1+, and 1−/1−. Later, Ball. S. P. et al.[7] analyzed the linkage in a DGI-II big family named Family MRC4000 with the polymorphic markers of GC and found that DGI-II had a close linkage with GC (Lod=+7.9, θ=0.13). In 1992, Crall et al.[8] mapped DGI-II to interval defined by two protein polymorphic markers: GC and interferon-inducible cytokine INP-10. The relative chromosome location was 4q12-21. The results above only offered a gross orientation of disease gene of DGI-II. Under that condition, it was almost impossible to clone the disease gene in this region.

In 1995, Crosby A.H et al[9] analyzed the linkage in two big DGI-II families with 9 short tandem repeat polymorphic markers (STRP) and mapped the disease gene to the 4q21-23 region defined by two STRPs of D4S2691 and D4S2692. Multipoints linkage analysis suggested that the disease gene might be in the region within about 3.2 cM around SPP1. Recently, Aplin H. M et al.[10] genotyped two big families used by Crosby A. H with 5 hyperdense STRPs. The linkage analysis showed that the disease gene of DGIII located between two STRPs of GATA62A11 and D4S1563 with a genetic distance of 2 cM. Moreover, this research group established the YACs Contigs in this region. They also identified that DMP1, IBSP, SPP1 and DSPP are all in this candidate region by PCR technology.

However, the mechanism of dentinogenesis imperfecta type II is still unclear so far. Also the direct relationship between dentinogenesis imperfecta type II and some special kind of protein is not reported.

In addition, there is still no effective method to diagnose DGI-II early and/or antenatally and to cure DGI-II by non-operative treatment in the art.

Therefore, there is an urgent need to develop new and efficient methods to diagnose and cure DGI-II, the relative pharmaceuticals, and diagnostic technology and reagents.

SUMMARY OF INVENTION

One purpose of the invention is to provide a new diagnostic method and detection kit, especially for antenatal and/or early diagnosis of dentinogenesis imperfecta type II (DGI-II) and dentinogenesis imperfecta type II with deafness (DGI-II with deafness).

Another purpose is to provide a new method to treat DGI-II and DGI-II with deafness.

Still another purpose is to provide a pharmaceutical composition to treat DGI-II and DGI-II with deafness.

In the first aspect, the invention provides a method for determining the susceptibility of DGI-II and/or DGI-II with deafness in a subject comprising the steps of:
  detecting the DSPP gene, transcript and/or protein in said subject and comparing it with the normal DSPP gene, transcript and/or protein to determine whether there is any difference,
  wherein said difference indicates that the possibility of suffering DGI-II and/or DGI-II with deafness in said subject is higher than the normal population.

In a preferred embodiment, the DSPP gene or transcript is detected, and compared with the normal DSPP nucleotide sequence to determine the difference. More preferably, said difference is selected from the group consisting of: in position 1 of Exon 3, G1→T1; in position 1 of Intron 3, G1→A1.

In the second aspect, the invention provides a method for treating DGI-II and/or DGI-II with deafness comprising the step of administrating a safe and effective amount of normal DSPP and/or DSP protein to the patient in need of said treatment. Preferably, the DSPP and/or DSP protein are administrated topically to periodontal tissues.

In the third aspect, the invention provides a pharmaceutical composition comprising a safe and effective amount of DSPP and/or DSP protein and a pharmaceutically acceptable carrier. Preferably, said pharmaceutical composition is injection.

In the fourth aspect, the invention provides a kit for detecting DGI-II and/or DGI-II with deafness comprising the primers which specifically amplify the DSPP gene or transcript. Preferably, the kit further comprises a probe that binds to the site of mutation.

In view of the technical teaching of the invention, the other aspects of the invention will be apparent to the skilled in the art.

DESCRIPTION OF DRAWINGS

FIG. 4A and 4B show mutations in DSPP gene. FIG. 4A shows G1→T1 in position 1 of Exon 3, which causes codon GTT change into TTT, resulting in a corresponding amine acid change of Val→Phe. The change of splicing site is shown in SEQ ID NO: 45, wherein n is G or T. A part of DSPP amino acid sequence is shown in SEQ ID NO: 47. FIG. 4B shows G1→A1 in position 1 of Intron 3, which causes the mutation of splicing site. The change of splicing site is shown in SEQ ID NO: 46, wherein n is A or G. A part of DSPP amino acid sequence is shown in SEQ ID NO: 48.

DETAILED DESCRIPTION OF INVENTION

Figure 1:
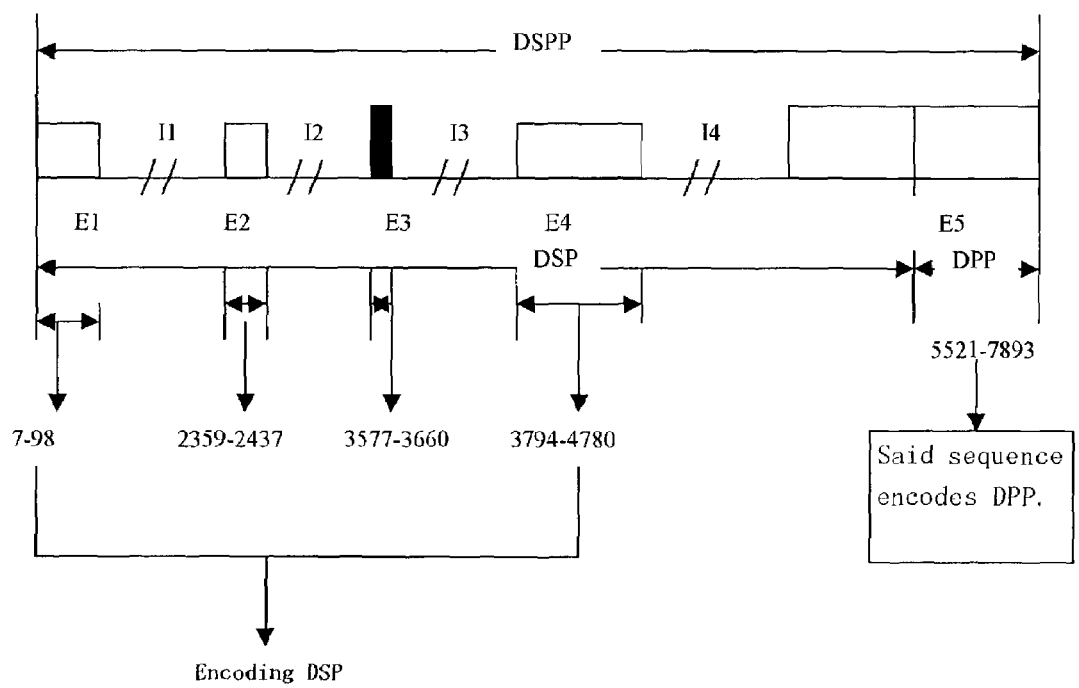
FIG. 1 shows the gene structure of DSPP. This gene contains 5 exons and 4 introns. The full length is 8210 bp. Exon 1 (7-98), Exon 2 (2359-2437), Exon 3 (3577-3660), Exon 4 (3794-4780) and Exon 5 (5257-8201) encode DSPP. Exons 1-4 and part of Exon 5 (5257-5520) encode DSP, while another part of Exon 5 (5521-7893) encodes DPP.

After studying for several years, the inventors of the invention have, for the first time found and proved dentin sialophosphoprotein (DSPP) and/or dentin sialoprotein (DSP) have a close relationship with dentinogenesis imperfecta type II (DGI-II). In addition, the new function of DSPP/DSP was found, i.e., the changes of DSPP or DSP will cause DGI-II directly. Based on this discovery, the inventors accomplished the invention.

Firstly, the inventors collected two genetic families affected by dentinogenesis imperfecta or dentinogenesis imperfecta with progressive hearing loss in China. Then they localized the disease gene of dentinogenesis imperfecta to the 4q21-22 region in Chromosome 4 by genotyping and linkage analysis with microsatellite markers Then, the inventors identified the candidate genes by the following steps:

(1) Finding all of the genes mapped in 4q21-22 region, i.e., making the transcription map in 4q21-22 region;

(2) Checking the expression situation of all of the genes in 4q21-22 region;

(3) Determining the genes mapped in 4q21-22 region and expressed in dental pulp as the candidates for dentinogenesis imperfecta.

The results showed that the candidate genes included DMP1, IBSP, SPP1, DSP, DPP and DSPP.

Further, the inventors used PCR-SSCP technique to screen all candidate genes for mutation and found that the mutations in DSPP have a direct causality with dentinogenesis imperfecta, while other genes do not.

Finally, the mode and site of DSPP mutation in two genetic families were identified by sequence analysis. In DGI-II family, sequencing revealed a G1→T1 mutation at position 1 of Exon 3 (position 3577 in SEQ ID NO:1). The mutation results in not only an amino acid change, but also a splicing site change which may cause the expression of intron, termination of translation in advance or frame shifting (FIG. 4A). Therefore, the normal DSPP (or DSP) protein is unable to be expressed.

In another DGI-II with deafness family, the mutation is a G1→A1 mutation in position 1 of Intron 3 (position 3661 of SEQ ID NO:1). The mutation was predicted to result in splicing site change, which may cause the expression of intron, termination of translation in advance or frame shifting (FIG. 4B). Therefore, the normal DSPP (or DSP) protein is unable to be expressed. Further, it may influence the translation of signal peptide so that DSPP can not be correctly localized. Surprisingly, this mutation causes the patient affected with both DGI-II and deafness, suggesting that DSPP mutation is associated with deafness. It is possible to diagnose deafness, especially DGI-II with deafness, by detecting whether DSPP is normal or not.

On the basis of this invention, one can design and exploit new drugs based on DSPP gene and its products (e.g., transcripts and proteins) as well as the interacting molecule. In addition, one can use DSPP gene in vitro to reconstruct teeth or remodel some tooth structure, such as dentin.

Human DSPP mutation causes human dentinogenesis imperfecta type II. Based on the DSPP gene and its expression products, one can develop new drugs and diagnosis/treatment techniques for detecting and treating human DGI-II.

Human DSPP Gene and Protein

The detailed sequences of human DSPP gene and protein are available in Genbank (The accession number is AF163151) and some references, such as Gu, K., Chang, S., Ritchie, H. H., Clarkson, B. H. and Rutherford, R. B., Eur. J. Oral Sci. 2000 Feb: 108 (1):35-42. In Sequence Listing, human DSPP nucleotide sequence and amino acid sequence are shown in SEQ ID NO:1 and SEQ ID NO: 2, respectively. FIG. 1 shows the introns and exons of human DSPP.

| | |
|---|---|
| Exon 1 | 7-98 |
| mRNA | join (7-98, 2359-2437, 3577-3660, 3794-4780, 5257-8201) |
| Exon 2 | 2359-2437 |
| CDS | join (2387-2437, 3577-3660, 3794-4780, 5257-7896) |
| sig_peptide | 2387-2431 |
| mat_peptide | join (2432-2437, 3577-3660, 3794-4780, 5257-7893)/ Product "DSPP" |
| mat_peptide | join (2432-2437, 3577-3660, 3794-4780, 5257-5520)/ Product "DSP" |
| Exon 3 | 3577-3660 |
| Exon 4 | 3794-4780 |
| Exon 5 | 5257-8201 |
| mat_peptide | 5521-7893 |
| misc_feature | 5596-5604 /note = "Region: cell binding domain" |
| PolyA_signal | 7988-7993 |
| PolyA_signal | 8171-8176 |

The DSPP and/or DSP protein or polypeptide have various uses including but not limited to: curing disorders caused by low or no activity of DSPP and/or DSP protein (using directly as a medicine), and screening out antibodies, polypeptides or ligands which promote the function of DSPP and/or DSP. The expressed recombinant DSPP and/or DSP protein can be used to screen polypeptide library to find therapeutically valuable polypeptide molecules which activate the function of DSPP and/or DSP protein.

In another aspect, the invention also includes polyclonal and monoclonal antibodies, preferably monoclonal antibodies, which are specific for polypeptides encoded by human DSPP DNA or fragments thereof. By "specificity", it is meant an antibody that binds to the human DSPP gene products or fragments thereof. Preferably, the antibody binds to the human DSPP gene products or fragments thereof and does not substantially recognize nor bind to other antigenically unrelated molecules. Antibodies that bind to human DSPP and block human DSPP protein and those which do not affect the human DSPP function are included in the invention.

The present invention includes not only intact monoclonal or polyclonal antibodies, but also immunologically-active antibody fragments, e.g., a Fab' or (Fab)$_2$ fragment, an antibody heavy chain, an antibody light chain, a genetically engineered single chain Fv molecule (Lander, et al., U.S. Pat. No. 4,946,778), or a chimeric antibody, e.g., an antibody which contains the binding specificity of a murine antibody, but the remaining portion of which is of human origin.

The antibodies in the present invention can be prepared by various techniques known to those skilled in the art. For example, purified human DSPP gene products, or its antigenic fragments can be administrated to animals to induce the production of polyclonal antibodies. Similarly, cells expressing human DSPP or its antigenic fragments can be used to immunize animals to produce antibodies. The antibodies of the invention can be monoclonal antibodies which can be prepared by using hybridoma technique (See Kohler, et al., Nature, 256; 495,1975; Kohler, et al., Eur. J. Immunol. 6: 511,1976; Kohler, et al., Eur. J. Immunol 6: 292, 1976; Hammerling, et al., In Monoclonal Antibodies and T Cell Hybridomas, Elsevier, N.Y., 1981). Antibodies of the invention comprise those which block human DSPP function and those which do not affect human DSPP function. Antibodies in the invention can be produced by routine immunology techniques and using fragments or functional regions of human DSPP gene product. These fragments and functional regions can be prepared by recombinant methods or synthesized by a polypeptide synthesizer. The antibodies binding to unmodified human DSPP gene product can be produced by immunizing animals with gene products produced by prokaryotic cells (e.g., *E. coli*), and the antibodies binding to post translationally modified forms thereof (e.g., glycosylated or phosphorylated polypeptide) can be acquired by immunizing animals with gene products produced by eukaryotic cells (e.g., yeast or insect cells).

The antibody against human DSPP and/or DSP protein can be used in immunohistochemical method to detect the presence of DSPP and/or DSP protein in the biopsy specimen.

The polyclonal antibodies can be prepared by immunizing animals, such as rabbit, mouse, and rat, with human DSPP and/or DSP protein. Various adjuvants, e.g., Freund's adjuvant, can be used to enhance the immunization.

The substances that act with DSPP and/or DSP protein, e.g., inhibitors, agonists and antagonists, can be screened out by various conventional techniques, using the protein of the invention.

The protein, antibody, inhibitor, agonist or antagonist of the invention provides different effects when administrated in therapy. Usually, these substances are formulated with a non-toxic, inert and pharmaceutically acceptable aqueous carrier. The pH typically ranges from 5 to 8, preferably from about 6 to 8, although pH may alter according to the property of the formulated substances and the diseases to be treated. The formulated pharmaceutical composition is administrated in conventional routine including, but not limited to, intramuscular, intravenous, subcutaneous, or topical administration. The topical administration at periodontal tissues is preferred.

The normal DSPP and/or DSP can be directly used for curing disorders, e.g., DGI-II. The DSPP and/or DSP protein of the invention can be administrated in combination with other medicaments for DGI-II.

The invention also provides a pharmaceutical composition comprising safe and effective amount of DSPP and/or DSP protein in combination with a suitable pharmaceutical carrier. Such a carrier includes but is not limited to saline, buffer solution, glucose, water, glycerin, ethanol, or the combination thereof. The pharmaceutical formulation should be suitable for the delivery method. The pharmaceutical composition of the invention may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., from about 1ug to 5 mg per kg body weight per day. Moreover, the polypeptide of the invention can be administrated together with other therapeutic agents.

When using pharmaceutical composition, the safe and effective amount of the DSPP and/or DSP protein or its antagonist or agonist is administrated to mammals. Typically, the safe and effective amount is at least about 0.1 ug/kg body weight and less than about 10 mg/kg body weight in most cases, and preferably about 0.1-100 ug/kg body weight. Of course, the precise amount will depend upon various factors, such as delivery methods, the subject health, and the like, and is within the judgment of the skilled clinician.

The human DSPP and/or DSP polynucleotides also have many therapeutic applications. Gene therapy technology can be used in the therapy of abnormal cell proliferation, development or metabolism, which is caused by the loss of DSPP and/or DSP expression or the expression of abnormal or non-active DSPP and/or DSP. The methods for constructing a recombinant virus vector harboring DSPP and/or DSP gene are described in the literature (Sambrook, et al.). In addition, the recombinant DSPP and/or DSP gene can be packed into liposome and then transferred into the cells.

The methods for introducing the polynucleotides into tissues or cells include: directly injecting the polynucleotides into tissue in the body, in vitro introducing the polynucleotides into cells with vectors, such as virus, phage, or plasmid, and then transplanting the cells into the body.

The invention further provides diagnostic assays for quantitative and in situ measurement of DSPP and/or DSP protein level. These assays are well known in the art and include FISH assay and radioimmunoassay. The level of DSPP and/or DSP protein detected in the assay can be used to illustrate the importance of DSPP and/or DSP protein in diseases and to determine the diseases associated with DSPP and/or DSP protein.

A method of detecting the presence of DSPP and/or DSP protein in a sample by utilizing the antibody specifically against DSPP and/or DSP protein comprises the steps of: contacting the sample with the antibody specifically against DSPP and/or DSP protein; observing the formation of antibody complex which indicates the presence of DSPP and/or DSP protein in a sample.

The polynucleotide encoding DSPP and/or DSP protein can be used in the diagnosis and treatment of DSPP and/or DSP protein related diseases. In respect of diagnosis, the polynucleotide encoding DSPP and/or DSP can be used to detect whether DSPP and/or DSP is expressed or not, and whether the expression of DSPP and/or DSP is normal or abnormal, e.g., in the case of diseases. DSPP DNA sequences can be used in the hybridization with biopsy samples to determine the expression of DSPP. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analyzing the differential expression of genes in tissues and for the diagnosis of genes. The DSPP and/or DSP specific primers can be used in RNA-polymerase chain reaction and in vitro amplification to detect the transcripts of DSPP and/or DSP.

Further, detection of the mutation of DSPP and/or DSP gene is useful for the diagnosis of DSPP and/or DSP protein related diseases. The mutation forms of DSPP and/or DSP include site mutation, translocation, deletion, rearrangement and any other mutations compared with the normal wild-type DSPP and/or DSP DNA sequence. The conventional methods, such as Southern blotting, DNA sequencing, PCR and in situ blotting, can be used to detect mutation. Moreover, mutation sometimes affects the expression of protein. Therefore, Northern blotting and Western blotting can be used to indirectly determine whether the gene is mutated or not.

The invention is further illustrated by the following examples. It is appreciated that these examples are only intended to illustrate the invention, but not to limit the scope of the invention. For the experimental methods in the following examples, they are performed under routine conditions, e.g., those described by Sambrook et al., in Molecule Clone: A Laboratory Manual, New York: Cold Spring Harbor Laboratory Press, 1989, or as instructed by the manufacturers, unless otherwise specified.

EXAMPLE 1

DGI-II family had 42 members, and DGI-II with deafness family had 14 members. All individuals were subjected to careful clinical examination and recorded in details by experienced dentists. The patients with deafness were examined carefully by otologists and identified by pure tone audiogram and brain stem evoked potential. 5 ml blood samples in the families were collected by standard venipuncture and stocked by ACD solution. DNA was extracted using the following method:

Preparation of Blood DNA Sample

Blood DNA samples were extracted by Qiagen kit according to manufacturer's instructions. The steps were as follows:

a. Add 20 ul Proteinase K, 200 ul blood sample and 200 ul Buffer AL into a 1.5 ml microcentrifuge tube. Mix by pulse-vortexing for 15 seconds.

b. Incubate for digestion at 56° C. for 10 minutes. Add 210 ul 100% ethanol to the sample, and briefly centrifuge for 10 seconds.

c. Carefully apply the mixture onto a QIAamp spin column and centrifuge at 8000 rpm for 1 minute.

d. Discard the filtrate and transfer the QIAamp spin column in another 2 ml collection tube.

e. Add 500 ul Buffer AW1 into QIAamp spin column, centrifuge at 8000 rpm for 1 minute.

f. Discard the filtrate and add 500 ul Buffer AW2 into QIAamp spin column, centrifuge at 14000 rpm for 3 minutes.

g. Discard the filtrate and place the QIAamp spin column in a new 1.5 ml microcentrifuge tube.

h. Add 200 ul Buffer AE into QIAamp spin column, incubate at room temperature for 5 minutes, and centrifuge at 8000 rpm for 1 minute. The filtrate collected in the tube was DNA solution from blood sample.

i. DNA quality was determined by 1% agarose gel electrophoresis. The DNA quantity was determined by UV spectrophotometer. The DNA samples were stored at −20° C.

EXAMPLE 2

1 Genotyping:

The sequences of high polymorphic STR markers in region 4q21 were obtained from Genome Database and markers A-G were D4S2691, D4S1534, GATA62μl 1, DSP, DMP1, SPP1, D4S451, respectively. PCR amplifications were carried out following LI-COR company manual for the touchdown program and using PTC-225 DNA Engine Tetrad (MJ-Research Inc.). PCR reactions were in 10 ul system containing 20 ng genomic DNA template, 2.0 mM dNTP, 1.0 pmol M13-tailed forward primer and reverse primer, 1.0 pmol fluorescent M13 primer, 1.5 mM $MgCl_2$, 10 mM Tris-HCl, and 1U AmpliTaq Gold Taq Polymerase (Perkin-Elmer Corp.). The reaction system was initially denatured at 95° C. for 8 minutes, followed by 4 cycles of denaturing at 95° C. for 45 seconds, annealing at 68° C. for 2 minutes with a drop of 2° C. per cycle until 60° C., and extending at 72° C. for 1 minute, and by a second set of 2-4 cycles of denaturing at 95° C. for 45 seconds, annealing at 58° C. for 1 minute with a drop of 2° C. per cycle until 50-54° C., and extending at 72° C. for 1 minute, and then by 20-30 cycles of denaturing at 95° C. for 30 seconds, annealing at 50-54° C. for 30 seconds and extending at 72° C. for 30 seconds. Finally the samples were extended at 72° C. for 15 minutes. PCR products and fluorescent-labeled standard size DNA markers were electrophoresed on a LI-COR automated sequencer on a polyacrylamide gel. Data were collected and analyzed by Base Image 4.1 and Gene Image 3.12 software, while linkage ready pedigree files were generated. These files were used for linkage analysis and haplotype analysis.

2. Linkage Analysis and Haplotype Analysis

DGI-II hereditary locus was modeled as an autosomal dominant inheritance with 100% penetrance in a two-allele system. The frequency of disease gene was set to 0.0001, the frequencies of STRs were assumed to be uniformly distributed. Two-point linkage analysis was performed by using MLINK and ILINK program from the LINKAGE version 5.10 software package. Haplotype construction was performed using SIMWALK2 version 2.31 and Cyrillic version 2.02 software.

Figure 2:
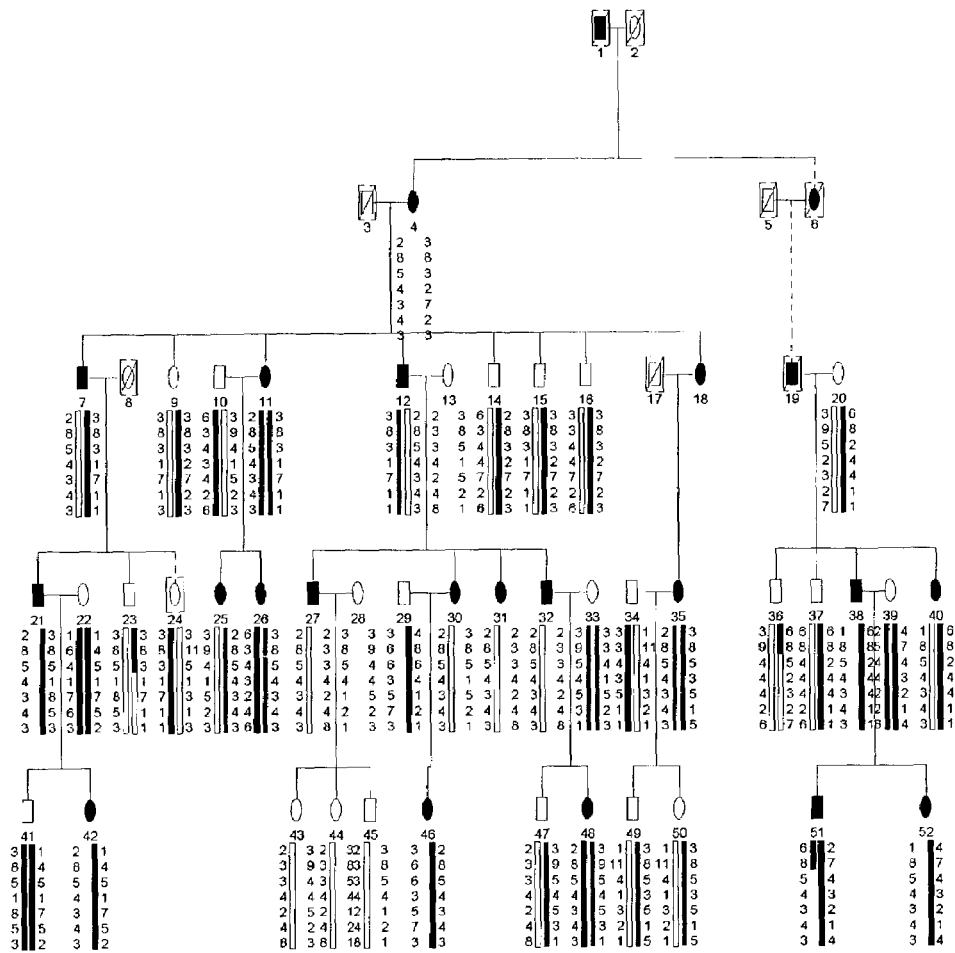
FIG. 2 shows the haplotype construction of STRP markers in 4q21 region in a dentinogenesis imperfecta type II family.
Figure 3:
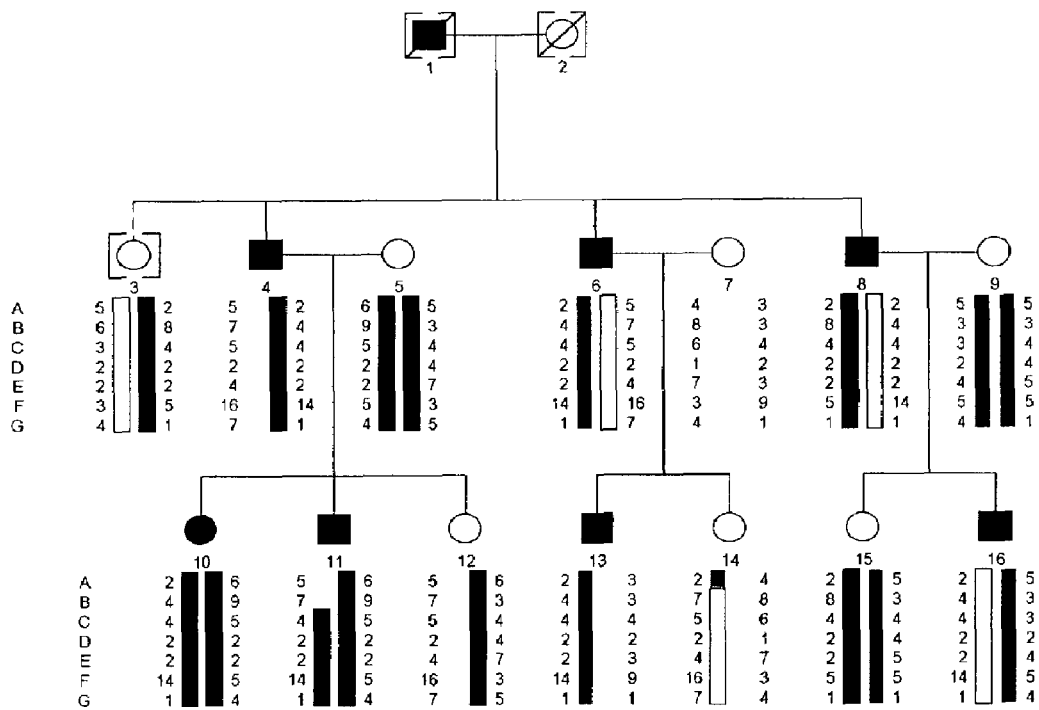
FIG. 3 shows the haplotype construction of STRP markers in 4q21 region in a DGI-II with deafness family. A square represents a male. A filled suuare represents a DGI-II or DGI-II with deafness male patient. An open square represent a normal male. A circle represents a female. A filled circle represents a DGI-II or DGI-II with deafness female patient. An open circle represents a normal female. A bracketed circle or square represents a person not affected by DGI-II or DGI-II with deafness but by other disease. A bracketed circle or sausre that is lined through represents a dead person. The long bars represent the same chromosome from different persons. The numbers adjacent to the bars represent markers.

The pedigree data are shown in Tables 1-2 and FIGS. 2-3.

TABLE 1

Disease locus in DGI-II pedigree and STRP two-point linkage analysis in 4q21 region

| Location | Lod score at θ | | | | | | | Maximum | |
|---|---|---|---|---|---|---|---|---|---|
| marker | 0.0 | 0.01 | 0.05 | 0.1 | 0.2 | 0.3 | 0.4 | Lod | θ |
| A | −∞ | −0.11 | 2.19 | 2.76 | 2.59 | 1.81 | 0.83 | 2.76 | 0.1 |
| B | 1.65 | 1.62 | 1.51 | 1.37 | 1.09 | 0.78 | 0.42 | 1.65 | 0.0 |
| C | 7.63 | 7.50 | 6.96 | 6.25 | 4.74 | 3.09 | 1.36 | 7.63 | 0.0 |
| D | 6.06 | 5.96 | 5.53 | 4.98 | 3.82 | 2.57 | 1.24 | 6.06 | 0.0 |
| E | 8.24 | 8.11 | 7.54 | 6.80 | 5.22 | 3.49 | 1.67 | 8.24 | 0.0 |
| F | 8.38 | 8.24 | 7.67 | 6.93 | 5.32 | 3.55 | 1.64 | 8.38 | 0.0 |
| G | 7.34 | 7.23 | 6.77 | 6.16 | 4.87 | 3.44 | 1.84 | 7.34 | 0.0 |

TABLE 2

Disease locus in DGI-II with deafness pedigree and Lod score in 4q21 region

| Location | Lod score at θ | | | | | | | Maximum | |
|---|---|---|---|---|---|---|---|---|---|
| marker | 0.0 | 0.01 | 0.05 | 0.1 | 0.2 | 0.3 | 0.4 | Lod | θ |
| A | −∞ | −2.86 | −1.48 | −0.92 | −0.42 | −0.18 | −0.05 | −0.05 | 0.4 |
| B | −∞ | 0.67 | 1.19 | 1.25 | 1.04 | 0.65 | 0.21 | 1.25 | 0.1 |
| C | 1.20 | 1.8 | 1.07 | 0.93 | 0.63 | 0.33 | 0.08 | 1.20 | 0.0 |
| D | −0.14 | −0.09 | −0.05 | −0.02 | −0.00 | −0.00 | −0.00 | −0.00 | 0.2 |
| E | 0.91 | 0.92 | 0.91 | 0.86 | 0.67 | 0.41 | 0.14 | 0.92 | 0.01 |
| F | 2.71 | 2.66 | 2.46 | 2.21 | 1.65 | 1.02 | 0.37 | 2.71 | 0.0 |
| G | 2.11 | 2.07 | 1.91 | 1.70 | 1.24 | 0.73 | 0.23 | 2.07 | 0.0 |

The results suggested that the disease genes in DGI-II and DGI-II with deafness pedigrees were linked with STRP markers in 4q21 region.

EXAMPLE 3

Mutation Screening of Candidate Genes

Using Primer 5.0 software, we designed primers to amplify exons and the splice junctions between exons and introns of DSP gene (Table 3). PCR-SSCP technique was used to screen DSP gene for mutation. PCR products were electrophoresed on 10% polyacrylamide gel and 9.3% polyacrylamide gel with 4% glycerol. Then, the gels were silver stained according to standard protocol.

Primers were as follows:

TABLE 3

| Primer Sequences in DSPP Coding Region | | | |
|---|---|---|---|
| Primer Name | Sequence | No. | bp |
| DSPP-E1 F | 5'-TGCAAAAGTCCATGACAGTG-3' | SEQ ID NO: 3 | 128 |
| DSPP-E1 R | 5'-TCAGTTGGTTCTGAGTAAAAGGA-3' | SEQ ID NO: 4 | |
| DSPP-E2 F | 5'-AAGTAATTTTGTGCTGTTCCTTT-3' | SEQ ID NO: 5 | 149 |
| DSPP-E2 R | 5'-AACAAAGTGAAGAGGTTTTCT-3' | SEQ ID NO: 6 | |

TABLE 3-continued

Primer Sequences in DSPP Coding Region

| Primer Name | Sequence | No. | bp |
|---|---|---|---|
| DSPP-E3 F | 5'-AAGAACCTTTTCAATTGCTAGT-3' | SEQ ID NO:7 | 189 |
| DSPP-E3 R | 5'-TGGAGAAGTTAATGGAATGTAGCA-3' | SEQ ID NO:8 | |
| DSPP-E4 F | 5'-TGCAATTTGCTTTCCTTCAA-3' | SEQ ID NO:9 | 205 |
| DSPP-E4 R | 5'-CCTCTTCGTTTGCTAATGTGG-3' | SEQ ID NO:10 | |
| DSPP-E5 F | 5'-TCACAAGGTAGAAGGGAATG-3' | SEQ ID NO:11 | 226 |
| DSPP-E5 R | 5'-GTTTGTGGCTCCAGCATTGT-3' | SEQ ID NO:12 | |
| DSPP-E6 F | 5'-GGGACACAGGAAAAGCAGAA-3' | SEQ ID NO:13 | 243 |
| DSPP-E6 R | 5'-TGTTATTGCTTCCAGCTACTTGAG-3' | SEQ ID NO:14 | |
| DSPP-E7 F | 5'-CAATGAGGATGTCGCTGTTG-3' | SEQ ID NO:15 | 206 |
| DSPP-E7 R | 5'-TATCCAGGCCAGCATCTTCT-3' | SEQ ID NO:16 | |
| DSPP-E8 F | 5'-CACCTCAGATCAACAGCAAGAG-3' | SEQ ID NO:17 | 226 |
| DSPP-E8 R | 5'-TCTTCTTTCCCATGGTCCTG-3' | SEQ ID NO:18 | |
| DSPP-E9 F | 5'-ATGAAGAAGCAGGGAATGGA-3' | SEQ ID NO:19 | 232 |
| DSPP-E9 R | 5'-ATTCTTTGGCTGCCATTGTC-3' | SEQ ID NO:20 | |
| DSPP-E10 F | 5'-TGATGGAGACAAGACCTCCAA-3' | SEQ ID NO:21 | 205 |
| DSPP-E10 R | 5'-TGCCATTGAAAGAAATCAGC-3' | SEQ ID NO:22 | |
| DSPP-E11 F | 5'-TTCTTTCCTCCATCCTTCCA-3' | SEQ ID NO:23 | 194 |
| DSPP-E11 R | 5'-TTCTGATTTTTGGCCAGGTC-3' | SEQ ID NO:24 | |
| DSPP-E12 F | 5'-GGCAATGTCAAGACACAAGG-3' | SEQ ID NO:25 | 236 |
| DSPP-E12 R | 5'-TCTCCTCGGCTACTGCTGTT-3' | SEQ ID NO:26 | |
| DSPP-E13 F | 5'-TGCAAGGAGATGATCCCAAT-3' | SEQ ID NO:27 | 231 |
| DSPP-E13 R | 5'-TGTCATCATTCCCATTGTTACC-3' | SEQ ID NO:28 | |
| DSPP-E14 F | 5'-CAAAAGGAGCAGAAGATGATGA-3' | SEQ ID NO:29 | 243 |
| DSPP-E14 R | 5'-TGCTGTCACTGTCACTGCTG-3' | SEQ ID NO:30 | |
| DSPP-E15 F | 5'-GCAGTGATAGTAGTGACAGCAGTG-3' | SEQ ID NO:31 | 205 |
| DSPP-E15 R | 5'-TTGCTGCTGTCTGACTTGCT-3' | SEQ ID NO:32 | |
| DSPP-E16 F | 5'-CAAATCAGACAGTGGCAAAGG-3' | SEQ ID NO:33 | 508 |
| DSPP-E16 R | 5'-GCTCTCACTGCTATTGCTGCT-3' | SEQ ID NO:34 | |
| DSPP-E17 F | 5'-GCAAGTCAGACAGCAGCAAA-3' | SEQ ID NO:35 | 598 |
| DSPP-E17 R | 5'-CTGCTGTCGCTATCACTGCT-3' | SEQ ID NO:36 | |
| DSPP-E18 F | 5'-ATAGCAACGACAGCAGCAAT-3' | SEQ ID NO:37 | 583 |
| DSPP-E18 R | 5'-TCGCTGCTATTGCTATCACTG-3' | SEQ ID NO:38 | |
| DSPP-E19 F | 5'-GCAACAGCAGTGATAGTGACA-3' | SEQ ID NO:39 | 598 |
| DSPP-E19 R | 5'-CTGCTGTCGCTGCTTTCA-3' | SEQ ID NO:40 | |
| DSPP-E20 F | 5'-AGCAGCGACAGCAGTGATAT-3' | SEQ ID NO:41 | 500 |
| DSPP-E20 R | 5'-TTGTTACCGTTACCAGACTTGC-3' | SEQ ID NO:42 | |
| DSPP-E21 F | 5'-TGACAGCACATCTGACAGCA-3' | SEQ ID NO:43 | 261 |
| DSPP-E21 R | 5'-TCCCCCAGTTGTTTTGTTT-3' | SEQ ID NO:44 | |

PCR products were sequenced to determine the type and location of mutations.

1. The DNA fragments that showed a changed electrophoresis pattern in SSCP analysis were amplified by standard PCR.
2. PCR products were purified with Millipore spin column.
3. Sequencing Reaction:

| (1) | Reaction system | |
|---|---|---|
| | Reaction mixture | 2 ul |
| | Primers (0.8 mM) | 2 ul |
| | Purified PCR products | 3 ul |
| (2) | Reaction conditions: | |
| | 96° C. | 30 sec |
| | 96° C. | 30 sec |
| | 50° C. | 5 sec |
| | 60° C. | 4 min |
| | 60° C. | 4 min |

Total 35 cycles (3) Precipitation of the Product of Sequencing Reaction

Add 9 volumes of 70% ethanol into the sequencing product, incubate at 4° C. for 3 minutes.

Centrifuge at 4° C. at 4000 rpm for 30 minutes.

Place the centrifuge tube upside down and continue to centrifuge until the speed reaches 1300 rpm at 4° C.

(4) Loading and Sequencing Samples

Add 2 ul Loading Dye buffer into precipitated products of sequencing reaction.

Incubate at 90° C. for 2 minutes and place it on ice immediately.

Load samples into ABI PRISM automated DNA sequencer to sequence.

The sequencing results were shown in FIGS. 4A and 4B. In DGI-II family, sequencing revealed a G1→T1 mutation at position 1 of Exon 3 (position 3577 in SEQ ID NO:1). This mutation resulted in not only an amino acid change, but also a splicing site change that might cause the expression of intron, termination of translation in advance or frame shifting (FIG. 4A). Therefore, the normal DSPP (or DSP) protein was unable to be expressed.

In another DGI-II with deafness family, the mutation was a G1→A1 mutation in position 1 of Intron 3 (position 3661 of SEQ ID NO:1). This mutation was predicted to result in splicing site change which may cause the expression of intron, termination of translation in advance or frame shifting (FIG. 4B). Therefore, the normal DSPP (or DSP) protein was unable to be expressed. Further, it might influence the translation of signal peptide so that DSPP could not be correctly localized. Surprisingly, this mutation caused the patient affected with both DGI-II and deafness, suggesting that DSPP mutation was associated with deafness. It is possible to diagnose deafness, especially DGI-II with deafness, by detecting whether DSPP is normal or not.

Discussion

1. Linkage and Haplotype Analysis

We used seven STR markers in 4q21 region to genotype DGI-II and DGI-II with deafness families. Linkage and haplotype construction showed that the disease gene in DGI-II family was linked with 4q21 and the maximum LOD score was 8.38 at SPP1 locus (θ=0.00) (Table 1, FIG. 2) and the disease gene in DGI-II with deafness was also linked with STR markers in 4q21 region and the maximum LOD score was 2.71 (θ=0.00) (Table 2, FIG. 3).

2. Mutation Screening of Candidate Genes and Confirmation by Sequencing

We designed 22 primers overlapping the DSPP gene to screen for mutations and identify mutations by sequencing. We found the disease gene in DGI-II family was linked with the STR markers in 4q21 region, while the disease gene in DGI-II with deafness was also linked with STR markers in this region. These mutations were not observed in 100 normal and unaffected individuals. It suggests that these mutations should be the cause of DGI-II disease.

DPP and DSP are two small polypeptides which have specific chemical properties and are cleaved from a single transcripts of DSPP gene. Both of them are expressed specifically in dental pulp tissue and may also be expressed in cochleae. DSP is a Glu-, Ser- and Gly-rich protein with many phosphorylation sites, which are predicted to be involved in dentin mineralization. DPP affects mineralization in two ways. Low concentration of DPP protein is able to bind to interspace of collagen I and initiate formation of phosphorum apatite crystals, while high concentration of DPP protein binds to the growing crystals, affects the size and form of crystals, and decreases the growth of crystals. It is necessary to further study the mechanism that the mutations in DSPP gene cause dentinogenesis imperfecta and deafness.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

REFERENCES

1. Witkop C J et al. Hereditary defects in enamel and dentin. Acta Genet 1957;7:236~239
2. Cetta G et al. Third international conference on osteogenesis imperfecta. Ann NY Avad Sci, 1998
3. Takagi Y et al. Matrix protein difference between human normal and dentinogenesis imperfecta dentin. In the chemistry and biology of mineralized connective tissues. Veis A, editor, New York: Elsevier/North-Holand. 1981
4. Witkop C J, et al. Medical and dental findings in the Brandywine isolate. AL J Med Sci 1966;3:382~403
5. Bixler D, et al. Dentinogenesis imperfecta: genetic variation in a six-generation family. J. Dent. Res. 1968;48: 1196~1199
6. Mikkelsen, M et al. Possible localization of Gc-system on chromosome 4. Loss of long arm 4 material associated with father-child incompatibility within the Gc-system. Hum. Hered. 1988;27: 105~107
7. Ball. S P, et al. Linkage between dentinogenesis imperfecta and Gc. Ann. Hum. Genet. 1982;46:35~40
8. Crall M G. Genetic marker study of dentinogenesis imperfecta. Proc Finn Dent Soc. 1992;88:285~293
9. Crodby A H, et al. Genetic mapping of dentinogenesis imperfecta type II Locus. Am. J. Hm. Genet. 1995;57: 832~839
10. Aplin H. M, et al. Refinement of the dentinogenesis imperfecta type II locus to an interval of less than 2 centimorgans at chromosome 4q21 and the creation of a yeast artificial chromosome contig of the critical region. J. Dent. Res. 1999;78(6):1270~1276

What is claimed is:

1. A method for determining the susceptibility of dentinogenesis imperfecta type II (DGI-II) and/or DGI-II with deafness in a human subject comprising the steps of:
   detecting the dentin sialophosphoprotein (DSPP) gene or transcript in said subject and comparing it with the wild-type DSPP gene or transcript thereof to determine whether there is any difference between the DSPP gene or transcript in said subject and the wild-type DSPP gene or transcript, wherein the wild-type gene comprises a nucleotide sequence of SEQ ID NO:1 and the wild-type transcript comprises nucleotides 7-98, 2359-2437, 3577-3660, 3794-4780, and 5257-8201 of SEQ ID NO: 1,
   wherein said difference comprises a G→T mutation at position 1 of Exon 3 or a G→A mutation at position 1 of Intron 3, and wherein said G→T mutation at position 1 of Exon 3 indicates an increased likelihood of suffering DGI-II in said subject and said G→A mutation at position 1 of Intron 3 indicates an increased likelihood of suffering DGI-II with deafness in said subject.

2. The method of claim 1 wherein the DSPP gene in said subject is detected, and compared with the nucleotide sequence of the wild-type DSPP to determine the difference.

3. A method of detecting dentinogenesis imperfecta type II (DGI-II) and/or DGI-II with deafness in a human subject, comprising:
   detecting a dentin sialophosphoprotein (DSPP) gene or transcript in said subject and comparing it with a wild-type DSPP gene or transcript to determine whether there is any difference between the DSPP gene or transcript in said subject and the wild-type DSPP gene or transcript, wherein the wild-type gene comprises a nucleotide sequence of SEQ ID NO: 1 and the wild-type transcript comprises nucleotides 7-98, 2359-2437, 3577-3660, 3794-4780, and 5257-8201 of SEQ ID NO: 1,
   wherein said difference comprises a G→T mutation at position 1 of Exon 3 or a G→A mutation at position 1 of Intron 3, and wherein said G→T mutation at position 1 of Exon 3 indicates DGI-II and said G→A mutation at position 1 of Intron 3 indicates DGI-II with deafness.

4. The method of claim 3, wherein the DSPP gene or transcript is detected with a primer or probe.

5. The method of claim 4, wherein the primer or probe detects a difference selected from the group consisting of:
   in position 1 of Exon 3, G1→T1; and
   in position 1 of Intron 3, G1→A1.

* * * * *

SEQUENCE LISTING

<160> NUMBER OF SEQ ID NOS: 44

<210> SEQ ID NO 1
<211> LENGTH: 8201
<212> TYPE: DNA
<213> ORGANISM: Homo sapiens

<400> SEQUENCE: 1

-continued

| | |
|---|---|
| attgtcatgc aaaagtccag gacagtgggc cactttcagt cttcaaagag aaagataaga | 60 |
| aattctggat tttcaaaatc cttttgaagc cttttaaggt aagatgaaat atccttttta | 120 |
| ctcagaacca actgattcat ttagaaagaa ctttgaattt caaagatgaa gccagtttga | 180 |
| ttttaagaag cgagtacccc ttaatgatta gattgtatgc ttccttttg acttgtcata | 240 |
| ttgatagtat gtataaaaga taacggacga ttacgaccta aggaagagat agattgggaa | 300 |
| gaagaaagac ctcgtactga aaaattggcc aactgaggtg gaaatttgac aattaactat | 360 |
| ctgggcactt tgattagttt tgataaaaaa tgagataact cagatttcaa aaatccacct | 420 |
| tgggctttca aacaaggctt caattaggct ttgctttta gtattttatt acttactatt | 480 |
| acttattatt tattgtccca catgaaatga aatttagcaa tcactaatga tgccaaatct | 540 |
| aattgctaaa tgaaatgaag ctaaatctca tttcattagt aacaataaat gaaataatct | 600 |
| gatggagctt cacaaattct gaagtctttg tttcatgctg aggtcacctg gccatttt | 660 |
| attgtagtct tcgaagtcat tcacctgcct tggaaacggt gataaccatc atggaattgt | 720 |
| tcaggagtgg agctgaaaga gagatgtagt ggtcagattt ctgaactgta gctcagaaac | 780 |
| tggacacgta tcactctggc cttggctgca ggtacctttc cagtatgctg aggctcttcc | 840 |
| aaatcacagt gcagacgggc cttctgcaga gctatgtaat gattaggctt gggactgcaa | 900 |
| agtacaggat aactgtggct tagtaaacag ctggccttca acatctgtgc cccagagctc | 960 |
| tgcatgatac ttgtcctggt gtcacctcag cctcacttga atctatggca tttcagaagg | 1020 |
| agctctagct gttcttggct ttctgttgaa cagctataag aatgagcact ttttccctc | 1080 |
| tcagtagctc tggaactgtg tcatctctcc tgtgagaaaa cgccagtaat tctcatgaca | 1140 |
| gttgatattc agtgaagttt tattatattt tcactaccac cattaaattc aatcaaagcc | 1200 |
| attttatgac atgcagcatt ataatctata catctggtgg gagttcatga ataggagta | 1260 |
| aaactctcct ttctatcatt acttcaagaa atccaacttg caatataaat taatttttt | 1320 |
| actcacacag attataaaat gtctattcca acttatcaga aacatgtttt agaccatttc | 1380 |
| tgaatttgaa ttctaacagg gatgaagaat catgatttta gaagtcccat aaaataattg | 1440 |
| ctatcattta ttcaaaaatt gcaaagtgcc tgaagcaatg ctagatattg ctgatagtca | 1500 |
| taaatattta tcaacaacat tcagaaaacg ttttttctg tgctttgcat tggaatacaa | 1560 |
| taatcaccaa gacactctcc tgggcctcag gagcttacag gaaatcaggg caacacataa | 1620 |
| gtaactaggc aatttaaac agtgcaatgc gttaccagtg agacgtgcaa acttccttgg | 1680 |
| tataaaagg aaagagatac caaatacccct ttgaagtggc gtcagagagg gcgtctcaga | 1740 |
| gataattcta ccaaacttca ggataatcct gaggtgcagg tgttgttatt attccaggtg | 1800 |
| gagggataat aaacctactt aaatttctca agcttacaca gcaagtagca ggggtaacat | 1860 |
| ttgaacccag gtctctgaat acaaacccg tattctttcc actagcgtag gctccctcat | 1920 |
| gttagtaatt tctttctctt aaagtctggt atagctcaat tctatagatt tggagtaagg | 1980 |
| atgacaagtg ttttaccttt gaagcacaat ttcagcagaa ttagttagta cttgattaaa | 2040 |
| gctattcaga agagaaatag atgttttttac acccaagaat tgcagaagaa caagttaca | 2100 |
| gctatgccct ttgtacctat tatggtgttt tccttcattg gcacaggcag aaaaaaatct | 2160 |
| aggaagctac attagtgctg agcctggtga tgtccccata accacaccag gtatgttctg | 2220 |
| gaccatcgta tgtcttctcg tgttagatac atgcttcttg tccaggaaaa gggcaaatgc | 2280 |
| ttacacatca aaataatata gtactatgat ttcccttta cttttataagt aattttgtgc | 2340 |
| tgttcctttt ttatacagcc attgattatt attattccta aagaaaatga agataattac | 2400 |

```
atatttttgc atttgggcag tagcatgggc cattccagta agtatgcctt tcttagaaaa    2460
cctcttcact tgttatctt ttttaaccta acattaatac aaaatgtagt gtgtgtgtgt    2520
gtgtgtgtgt gtgtgtgtgt gtgcatgtac atgtgtgtat atatgtgtgt gtgtatatat    2580
gtttccttaa ttttttttaa caggctgagt ctaaacattt agatttgcac taagggcttt    2640
atgtgatatc tgtgaggttt caacaaaacc actccaattc atcgtctcat tcctctatag    2700
aaactcatat ctcgtctgaa ggattattat tatttaaaac atttattcag attaatttac    2760
acttaatgcc cagaagtcat ggagactttg tccatctttg cttcatactc tgtgaatttc    2820
attctaatac gaacaaagtc tgtgctgttt aggaagtttc caagaaagaa taataagaaa    2880
aagtagattt ttttttcaaca tataggagac taatttttca ctcagagtta ttatttatgt    2940
gctcactgtg gaaaatttgg aatatatgac gaaaaccaat aaaaaattga gaaaattcaa    3000
ccatttataa ttttactagc cagccatcat gtttaacatt ttcatatgct ttcataatac    3060
caaacatttg gtatttatgt agttgaaaat gttctcaagt atttcaaatg tgctcttgca    3120
gagcacagaa gtatactagc gtaatacttg attttgcttc tgtgcaggct ctggtcacgc    3180
ctcctgttct cttaagagtt ttcatcagga ttacacttag agcgggtttg tgctagtgca    3240
agaggctttt tgtagagaaa caccagaggt ctatcccctc gtctttctac aagactcttt    3300
ccttctacag ttgagataag tgggctgatc taacacgtcc ataaaattgg taataccaca    3360
gtgaaaaata tccatgtacc cagtttaaat tctacacaag ccctgtaaga agccacttct    3420
cttttctatc tgattagatc atactttggc ctttgtgtta aaccttttctt cttcatggag    3480 ggaagaatat ttgtgtgtgt gtgtgtgtgt gtgcacgctc acacacatat tcacaaataa    3540
gaaccttttc aatagccagt attttctact tggcaggttc ctcaaagcaa accactggag    3600
agacatgtcg aaaaatccat gaatttgcat ctcctagcaa gatcaaatgt gtcagtacag    3660
gtataggatg taatatattt catttatt  cctatttctg agttgctaca ttccattaac    3720
ttctccaaga ttgcaatttg ctttccttca agatcattga cactcataat tgattgaatt    3780 gtttctttt caggatgagt taaatgccag tggaaccatc aaagaaagtg gtgtcctggt    3840
gcatgaaggt gatagaggaa ggcaagagaa tacccaagat ggtcacaagg gagaagggaa    3900
tggctctaag tgggcagaag taggagggaa gagttttttct acatattcca cattagcaaa    3960
cgaagagggg aatattgagg gctggaatgg ggacacagga aaagcagaaa catatggtca    4020
tgatggaata catgggaaag aagaaaacat cacagcaaat ggcatccagg gacaagtaag    4080
catcattgac aatgctggag ccacaaacag aagcaacact aatggaaata ctgataagaa    4140
tacccaaaat ggggatgttg gcgatgcagg tcacaatgag gatgtcgctg ttgtccaaga    4200
agatggacct caagtagctg gaagcaataa cagtacagac aatgaggatg aaataattga    4260
gaattcctgt agaaacgagg gtaatacaag tgaaataaca cctcagatca acagcaagag    4320
aaatgggact aaggaagctg aggtaacacc aggcactgga gaagatgctg gcctggataa    4380
ttccgatggg agtcctagtg ggaatggagc agatgaggat gaagacgagg gttctggtga    4440
tgatgaagat gaagaagcag ggaatggaaa agacagtagt aataacagca agggccagga    4500
gggccaggac catgggaaag aagatgatca tgatagtagc ataggtcaaa attcggatag    4560
taaagaatat tatgaccctg aaggcaaaga agatccccat aatgaagttg atggagacaa    4620
gacctccaag agtgaggaga attctgctgg tattccagaa gacaatggca gccaaagaat    4680
agaggacacc cagaagctca accatagaga aagcaaacgc gtagaaaata gaatcaccaa    4740
```

-continued

```
agaatcagag acacatgctg ttgggaagag ccaagataag gttagtttgt aaagctgatt      4800
tctttcaatg gcagtttaaa ttcttcccct ccatctattg atgctagcac aaaaataaac      4860
catgacaagc atccatgtat ttttgtatcc atattacttg actatttaag gaaatctaga      4920
gtccttacta gacttcgaga tagaacaact ttaaacatct tacatttctg ataacttagt      4980
tataattcta gaaaagtctt atgtgaaatc atggatcccc atgtaattgt ttacaaaagt      5040
tcctactggg taggaatgtg gatgaatttt taaggaatct aagcaccagg atgctttcaa      5100
ttacagaata aagcacattt tcacaaataa ctgtgaagta ctagaaatgt aactcctatc      5160
cctatggcaa cttttcccag ttattcttcc tcagatcaat gcaattttgc agcaaatatt      5220
cactagttaa tcattctttc ctccatcctt ccatagggaa tagaaatcaa gggtcccagc      5280
agtggcaaca gaaatattac caaagaagtt gggaaaggca acgaaggtaa agaggataaa      5340
ggacaacatg gaatgatctt gggcaaaggc aatgtcaaga cacaaggaga ggttgtcaac      5400
atagaaggac ctggccaaaa atcagaacca ggaaataaag ttggacacag caatacaggt      5460
agtgacagca atagtgatgg atatgacagt tatgattttg atgataagtc catgcaagga      5520
gatgatccca atagcagtga tgaatctaat ggcaatgatg atgctaattc agaaagtgac      5580
aataacagca gtagccgagg agatgcttct tataactctg atgaatcaaa agataatggc      5640
aatggcagtg actcaaaagg agcagaagat gatgacagtg atagcacatc agacactaat      5700
aatagtgaca gtaatggcaa tggtaacaat gggaatgatg acaatgacaa atcagacagt      5760
ggcaaaggta aatcagatag cagtgacagt gatagtagtg atagcagcaa tagcagtgat      5820
agtagtgaca gcagtgacag tgacagcagt gatagcaaca gtagcagtga tagtgacagc      5880
agtgacagtg acagcagtga tagcagtgac agtgatagta gtgatagcag caatagcagt      5940
gacagtagtg acagcagtga tagcagtgac agtagtgata gtagtgacag cagtgacagc      6000
aagtcagaca gcagcaaatc agagagcgac agcagtgata gtgacagtaa gtcagacagc      6060
agtgacagca acagcagtga cagtagtgac aacagtgata gcagcgacag cagcaatagc      6120
agtaacagca gtgatagtag tgacagcagt gatagcagtg acagcagcag tagcagtgac      6180
agcagcagta gcagtgacag cagcaacagc agtgatagta gtgacagtag tgacagcagc      6240
aatagcagtg agagcagtga tagtagtgac agcagtgata gtgacagcag tgatagtagt      6300
gacagcagta atagtaacag cagcgatagt gacagcagca acagcagcga tagcagtgac      6360
agcagtgata gcagtgacag cagcaacagc agtgacagta gcgatagcag tgacagcagc      6420
aacagcagtg acagcagtga tagcagtgac agcagtgata gtagtgacag cagcaacagc      6480
agtgatagca acgacagcag caatagcagt gacagcagtg atagcagcaa cagcagtgat      6540
agcagcaaca gcagtgatag cagtgatagc agtgacagca gtgatagcga cagcagcaat      6600
agcagtgaca gcagtaatag tagtgacagc agcgatagca gcaacagcag tgatagcagc      6660
gacagcagcg atagcagtga cagcagtgat agcgacagca gcaatagaag tgacagtagt      6720
aatagtagtg acagcagcga tagcagtgac agcagcaaca gcagtgacag cagtgatagt      6780
agtgacagca gtgacagcaa cgaaagcagc aatagcagtg acagcagtga tagcagcaac      6840
agcagtgata gtgacagcag tgatagcagc aacagcagtg acagcagtga tagcagcaac      6900
agcagtgata gcagtgaaag cagtaatagt agtgacaaca gcaatagcag tgacagcagc      6960
aacagcagtg acagcagtga tagcagtgac agcagtaata gtagtgacag cagcaatagc      7020
ggtgacagca gcaacagcag tgacagcagt gatagcaata gcagcgacag cagtgacagc      7080
agcaacagca gcgatagcag tgacagcagt gatagcagtg acagcagtga cagcagtgat      7140
```

-continued

```
agcagcaaca gcagtgatag cagtgacagc agtgacagca gtgatagcag taatagtagt     7200
gacagcagca acagcagtga cagcagcgat agcagtgaca gcagcgatag cagtgacagc     7260
agtgacagca gcaatagcag tgacagcagt gacagcagcg acagcagtga tagcagtgac     7320
agcagtggca gcagcgacag cagtgatagc agtgacagca gtgatagcag cgatagcagt     7380
gacagcagcg acagcagtga cagcagtgac agcagtgaaa gcagcgacag cagcgatagc     7440
agcgacagca gtgacagcag cgacagcagt gacagcagcg atagcagcga cagcagcgac     7500
agcagcgata gcgtgacagc cagcaatagc agtgatagca gcgacagcag tgatagcagt     7560
gacagcagcg acagcagcga tagcagcgac agcagtgata gtagtgatag cagtgacagc     7620
agtgacagca gcgacagcag tgacagcagc gacagcagtg acagcagcga cagcagtgac     7680
agcaatgaaa gcagcgacag cagtgacagc agcgatagca gtgacagcag caacagcagt     7740
gacagcagcg acagcagtga tagcagtgac agcacatctg acagcaatga tgagagtgac     7800
agccagagca agtctggtaa cggtaacaac aatggaagtg acagtgacag tgacagtgaa     7860
ggcagtgaca gtaaccactc aaccagtgat gattagaaca aagaaaaac ccataagatt     7920 cctttgtga aagtttggt aatgggatag gaaaaaaga tttccaagaa agtaaagaaa     7980
ggggagaaat aaacataaga cgtatgtaaa caaaaacaac tgggggaatc aaatcaaaca     8040
gttggattca gaaccaagac ctaactcctg cagagacaga ctctgaatgc atgacctttg     8100
gtacatgcct gttaatattc atgttctgaa aatattttgt taaaagtgta aatctaaaca     8160
taaaagaaca attaaaatat tctttaatac ttcacacaga a                        8201
```

<210> SEQ ID NO 2
<211> LENGTH: 1253
<212> TYPE: PRT
<213> ORGANISM: Homo sapiens

<400> SEQUENCE: 2

```
Met Lys Ile Ile Thr Tyr Phe Cys Ile Trp Ala Val Ala Trp Ala Ile
1               5                   10                  15

Pro Val Pro Gln Ser Lys Pro Leu Glu Arg His Val Glu Lys Ser Met
            20                  25                  30

Asn Leu His Leu Leu Ala Arg Ser Asn Val Ser Val Gln Asp Glu Leu
        35                  40                  45

Asn Ala Ser Gly Thr Ile Lys Glu Ser Gly Val Leu His Glu Gly
    50                  55                  60

Asp Arg Gly Arg Gln Glu Asn Thr Gln Asp Gly His Lys Gly Glu Gly
65                  70                  75                  80

Asn Gly Ser Lys Trp Ala Glu Val Gly Gly Lys Ser Phe Ser Thr Tyr
                85                  90                  95

Ser Thr Leu Ala Asn Glu Glu Gly Asn Ile Glu Gly Trp Asn Gly Asp
            100                 105                 110

Thr Gly Lys Ala Glu Thr Tyr Gly His Asp Gly Ile His Gly Lys Glu
        115                 120                 125

Glu Asn Ile Thr Ala Asn Gly Ile Gln Gly Gln Val Ser Ile Ile Asp
    130                 135                 140

Asn Ala Gly Ala Thr Asn Arg Ser Asn Thr Asn Gly Asn Thr Asp Lys
145                 150                 155                 160

Asn Thr Gln Asn Gly Asp Val Gly Asp Ala Gly His Asn Glu Asp Val
                165                 170                 175

Ala Val Val Gln Glu Asp Gly Pro Gln Val Ala Gly Ser Asn Asn Ser
```

-continued

```
                180                 185                 190
Thr Asp Asn Glu Asp Glu Ile Ile Glu Asn Ser Cys Arg Asn Glu Gly
        195                 200                 205
Asn Thr Ser Glu Ile Thr Pro Gln Ile Asn Ser Lys Arg Asn Gly Thr
    210                 215                 220
Lys Glu Ala Glu Val Thr Pro Gly Thr Gly Glu Asp Ala Gly Leu Asp
225                 230                 235                 240
Asn Ser Asp Gly Ser Pro Ser Gly Asn Gly Ala Asp Glu Asp Glu Asp
                245                 250                 255
Glu Gly Ser Gly Asp Asp Glu Asp Glu Ala Gly Asn Gly Lys Asp
            260                 265                 270
Ser Ser Asn Asn Ser Lys Gly Gln Glu Gly Gln Asp His Gly Lys Glu
        275                 280                 285
Asp Asp His Asp Ser Ser Ile Gly Gln Asn Ser Asp Ser Lys Glu Tyr
    290                 295                 300
Tyr Asp Pro Glu Gly Lys Glu Asp Pro His Asn Glu Val Asp Gly Asp
305                 310                 315                 320
Lys Thr Ser Lys Ser Glu Glu Asn Ser Ala Gly Ile Pro Glu Asp Asn
                325                 330                 335
Gly Ser Gln Arg Ile Glu Asp Thr Gln Lys Leu Asn His Arg Glu Ser
            340                 345                 350
Lys Arg Val Glu Asn Arg Ile Thr Lys Glu Ser Glu Thr His Ala Val
        355                 360                 365
Gly Lys Ser Gln Asp Lys Gly Ile Glu Ile Lys Gly Pro Ser Ser Gly
    370                 375                 380
Asn Arg Asn Ile Thr Lys Glu Val Gly Lys Gly Asn Glu Gly Lys Glu
385                 390                 395                 400
Asp Lys Gly Gln His Gly Met Ile Leu Gly Lys Gly Asn Val Lys Thr
                405                 410                 415
Gln Gly Glu Val Val Asn Ile Glu Gly Pro Gly Gln Lys Ser Glu Pro
            420                 425                 430
Gly Asn Lys Val Gly His Ser Asn Thr Gly Ser Asp Ser Asn Ser Asp
        435                 440                 445
Gly Tyr Asp Ser Tyr Asp Phe Asp Asp Lys Ser Met Gln Gly Asp Asp
    450                 455                 460
Pro Asn Ser Ser Asp Glu Ser Asn Gly Asn Asp Asp Ala Asn Ser Glu
465                 470                 475                 480
Ser Asp Asn Asn Ser Ser Arg Gly Asp Ala Ser Tyr Asn Ser Asp
                485                 490                 495
Glu Ser Lys Asp Asn Gly Asn Gly Ser Asp Ser Lys Gly Ala Glu Asp
            500                 505                 510
Asp Asp Ser Asp Ser Thr Ser Asp Thr Asn Asn Ser Asp Ser Asn Gly
        515                 520                 525
Asn Gly Asn Asn Gly Asn Asp Asn Asp Lys Ser Asp Ser Gly Lys
    530                 535                 540
Gly Lys Ser Asp Ser Ser Asp Ser Asp Ser Asp Ser Ser Asn Ser
545                 550                 555                 560
Ser Asp Ser Ser Asp Ser Ser Asp Ser Asp Ser Ser Asp Ser Asn Ser
                565                 570                 575
Ser Ser Asp Ser Asp Ser Ser Asp Ser Asp Ser Ser Asp Ser Ser Asp
            580                 585                 590
Ser Asp Ser Ser Asp Ser Ser Asn Ser Ser Asp Ser Ser Asp Ser Ser
        595                 600                 605
```

```
Asp Ser Ser Asp Ser Ser Asp Ser Ser Asp Ser Asp Ser Lys Ser
    610             615             620
Asp Ser Ser Lys Ser Glu Ser Asp Ser Ser Asp Ser Asp Ser Lys Ser
625             630             635             640
Asp Ser Ser Asp Ser Asn Ser Ser Asp Ser Ser Asp Asn Ser Asp Ser
                645             650             655
Ser Asp Ser Ser Asn Ser Ser Asn Ser Ser Asp Ser Ser Asp Ser
            660             665             670
Asp Ser Ser Asp Ser Ser Ser Ser Asp Ser Ser Ser Ser Asp
        675             680             685
Ser Ser Asn Ser Ser Asp Ser Ser Asp Ser Ser Asp Ser Asn Ser
    690             695             700
Ser Glu Ser Ser Asp Ser Ser Asp Ser Ser Asp Ser Ser Asp
705             710             715             720
Ser Ser Asp Ser Ser Asn Ser Asn Ser Ser Asp Ser Asp Ser Ser Asn
            725             730             735
Ser Ser Asp Ser Ser Asp Ser Asp Ser Ser Asp Ser Ser Asn Ser
        740             745             750
Ser Asp Ser Ser Asp Ser Ser Asp Ser Ser Asn Ser Ser Asp Ser Ser
    755             760             765
Asp Ser Ser Asp Ser Ser Asp Ser Ser Asp Ser Asn Ser Ser Asp
770             775             780
Ser Asn Asp Ser Ser Asn Ser Ser Asp Ser Ser Asp Ser Ser Asn Ser
785             790             795             800
Ser Asp Ser Ser Asn Ser Ser Asp Ser Ser Asp Ser Ser Asp Ser Ser
            805             810             815
Asp Ser Asp Ser Ser Asn Ser Ser Asp Ser Ser Asn Ser Ser Asp Ser
        820             825             830
Ser Asp Ser Ser Asn Ser Ser Asp Ser Ser Asp Ser Ser Asp Ser Ser
    835             840             845
Asp Ser Ser Asp Ser Asp Ser Ser Asn Arg Ser Asp Ser Ser Asn Ser
850             855             860
Ser Asp Ser Ser Asp Ser Ser Asp Ser Ser Asn Ser Ser Asp Ser Ser
865             870             875             880
Asp Ser Ser Asp Ser Ser Asp Ser Asn Glu Ser Ser Asn Ser Ser Asp
            885             890             895
Ser Ser Asp Ser Ser Asn Ser Ser Asp Ser Ser Asp Ser Ser
        900             905             910
Asn Ser Ser Asp Ser Ser Asp Ser Ser Asn Ser Ser Asp Ser Ser Glu
    915             920             925
Ser Ser Asn Ser Ser Asp Asn Ser Asn Ser Ser Asp Ser Ser Asn Ser
930             935             940
Ser Asp Ser Ser Asp Ser Ser Asp Ser Asn Ser Ser Asp Ser Ser
945             950             955             960
Asn Ser Gly Asp Ser Ser Asn Ser Ser Asp Ser Ser Asp Ser Asn Ser
            965             970             975
Ser Asp Ser Ser Asp Ser Ser Asn Ser Ser Asp Ser Ser Asp Ser Ser
        980             985             990
Asp Ser Ser Asp Ser Ser Asp Ser  Ser Asp Ser Ser Asn  Ser Ser Asp
    995                 1000              1005
Ser Ser  Asp Ser Ser Asp Ser  Ser Asp Ser Ser Asn  Ser Ser Asp
    1010               1015             1020
```

-continued

Ser Ser Asn Ser Ser Asp Ser Ser Asp Ser Ser Asp Ser Ser Asp
1025                1030                1035

Ser Ser Asp Ser Ser Asp Ser Ser Asn Ser Ser Asp Ser Ser Asp
    1040                1045                1050

Ser Ser Asp Ser Ser Asp Ser Ser Asp Ser Ser Gly Ser Ser Asp
    1055                1060                1065

Ser Ser Asp Ser Ser Asp Ser Ser Asp Ser Ser Asp Ser Ser Asp
    1070                1075                1080

Ser Ser Asp Ser Ser Asp Ser Ser Asp Ser Ser Glu Ser Ser Asp
    1085                1090                1095

Ser Ser Asp Ser Ser Asp Ser Ser Asp Ser Ser Asp Ser Ser Asp
    1100                1105                1110

Ser Ser Asp Ser Ser Asp Ser Ser Asp Ser Ser Asp Ser Ser Asp
    1115                1120                1125

Ser Ser Asn Ser Ser Asp Ser Ser Asp Ser Ser Asp Ser Ser Asp
    1130                1135                1140

Ser Ser Asp Ser Ser Asp Ser Ser Asp Ser Ser Asp Ser Ser Asp
    1145                1150                1155

Ser Ser Asp Ser Ser Asp Ser Ser Asp Ser Ser Asp Ser Ser Asp
    1160                1165                1170

Ser Ser Asp Ser Ser Asp Ser Ser Asp Ser Asn Glu Ser Ser Asp
    1175                1180                1185

Ser Ser Asp Ser Ser Asp Ser Ser Asp Ser Ser Asn Ser Ser Asp
    1190                1195                1200

Ser Ser Asp Ser Ser Asp Ser Ser Asp Ser Thr Ser Asp Ser Asn
    1205                1210                1215

Asp Glu Ser Asp Ser Gln Ser Lys Ser Gly Asn Gly Asn Asn Asn
    1220                1225                1230

Gly Ser Asp Ser Asp Ser Asp Ser Glu Gly Ser Asp Ser Asn His
    1235                1240                1245

Ser Thr Ser Asp Asp
    1250

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tgcaaaagtc catgacagtg                                          20

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
tcagttggtt ctgagtaaaa agga                                     24

<210> SEQ ID NO 5
<211> LENGTH: 23
<212> TYPE: DNA
<213> ORGANISM: Artificial Sequence
<220> FEATURE:
<223> OTHER INFORMATION: Primer

```
<400> SEQUENCE: 5
aagtaatttt gtgctgttcc ttt                                          23

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
aacaaagtga agaggttttc t                                            21

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
aagaaccttt tcaattgcta gt                                           22

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
tggagaagtt aatggaatgt agca                                         24

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgcaatttgc tttccttcaa                                              20

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
cctcttcgtt tgctaatgtg g                                            21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tcacaaggta gaagggaatg                                              20

<210> SEQ ID NO 12
```

```
<211> LENGTH: 20
<212> TYPE: DNA
<213> ORGANISM: Artificial Sequence
<220> FEATURE:
<223> OTHER INFORMATION: Primer

<400> SEQUENCE: 12
gtttgtggct ccagcattgt                                                    20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gggacacagg aaaagcagaa                                                    20

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
tgttattgct tccagctact tgag                                               24

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
caatgaggat gtcgctgttg                                                    20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tatccaggcc agcatcttct                                                    20

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
cacctcagat caacagcaag ag                                                 22

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
```
tcttctttcc catggtcctg    20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
atgaagaagc agggaatgga    20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
attctttggc tgccattgtc    20

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
tgatggagac aagacctcca a    21

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tgccattgaa agaaatcagc    20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ttctttcctc catccttcca    20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ttctgatttt tggccaggtc    20

<210> SEQ ID NO 25
<211> LENGTH: 20
<212> TYPE: DNA

<213> ORGANISM: Artificial Sequence
<220> FEATURE:
<223> OTHER INFORMATION: Primer

<400> SEQUENCE: 25
ggcaatgtca agacacaagg                                                    20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tctcctcggc tactgctgtt                                                    20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tgcaaggaga tgatcccaat                                                    20

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
tgtcatcatt cccattgtta cc                                                 22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
caaaaggagc agaagatgat ga                                                 22

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tgctgtcact gtcactgctg                                                    20

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
gcagtgatag tagtgacagc agtg                                               24

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ttgctgctgt ctgacttgct                                       20

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
caaatcagac agtggcaaag g                                     21

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
gctctcactg ctattgctgc t                                     21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gcaagtcaga cagcagcaaa                                       20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ctgctgtcgc tatcactgct                                       20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
atagcaacga cagcagcaat                                       20

<210> SEQ ID NO 38
<211> LENGTH: 21
<212> TYPE: DNA
<213> ORGANISM: Artificial Sequence
<220> FEATURE:

<223> OTHER INFORMATION: Primer

<400> SEQUENCE: 38
tcgctgctat tgctatcact g          21

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
gcaacagcag tgatagtgac a          21

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
ctgctgtcgc tgctttca          18

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
agcagcgaca gcagtgatat          20

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
ttgttaccgt taccagactt gc          22

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
tgacagcaca tctgacagca          20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
tcccccagtt gtttttgttt          20